United States Patent [19]

Li

[11] 4,081,434

[45] Mar. 28, 1978

[54] NOVEL ANALOGS OF β-ENDORPHIN

[75] Inventor: Choh Hao Li, Berkeley, Calif.

[73] Assignee: Hoffmann-La Roche Inc., Nutley, N.J.

[21] Appl. No.: 776,568

[22] Filed: Mar. 11, 1977

[51] Int. Cl.$^2$ .................... C07C 103/52; A61K 37/00
[52] U.S. Cl. ............................ 260/112.5 R; 424/177
[58] Field of Search ................................ 260/112.5 R

[56] References Cited

U.S. PATENT DOCUMENTS 4,038,222  7/1977  Li .................................. 260/112.5 R

OTHER PUBLICATIONS

G. Ungar, et al., Opiates and Endogenous Opioids Peptides, 1976, pp. 121-128.

D. H. Coy, et al., Biochem. and Biophys. Res. Commun. 73, 1976, pp. 632-638.

Primary Examiner—Delbert R. Phillips
Attorney, Agent, or Firm—Samuel L. Welt; Jon S. Saxe; George M. Gould

[57] ABSTRACT

Snythetic analogs of β-endorphin having the sequence β-endorphin-(1-5)-(16-31) are disclosed. These compounds are potent opiate agonists and analgesic agents, having activities in excess of the parent compounds. Moreover, the present analogs lack the antigenic determinent site which is believed to reside in residues 6-15 of β-endorphin. Thus the analogs present a substantially reduced risk of inducing an anaphylactic response in a treated individual.

7 Claims, No Drawings

NOVEL ANALOGS OF β-ENDORPHIN

DESCRIPTION OF THE INVENTION

The present invention relates to novel analogs of β-endorphin which analogs have the sequence β-endorphin-(1-5)-(16-31). These compounds are potent opiate agonists and analgesic agents and demonstrate an even higher activity than the parent compounds.

For the purpose of this disclosure the term β-endorphin is intended to encompass the various sequences which result from species variability. Thus β-endorphin will include, for example, β-endorphin having a sequence derived from human ($\beta_h$-endorphin), camel ($\beta_c$-endorphin) or porcine ($\beta_p$-endorphin) sources. These compounds have exhibited essentially equivalent levels of biological activity.

Thus, in particular, the present invention relates to the following specific compounds:

$\beta_h$-endorphin-(1-5)-(16-31)
$\beta_c$-endorphin-(1-5)-(16-31)
$\beta_p$-endorphin-(1-5)-(16-31)

The compounds of the invention can be conveniently prepared by solid phase synthesis following the procedure disclosed in U.S. patent application Ser. No. 677,747, filed Mar. 17, 1976, except that the amino acids contained in the residue 6-15 of β-endorphin are not included in the cycles.

It is within the scope of the present invention to substitute an amino acid having the D-configuration for an amino acid in the β-endorphin sequence during the solid synthesis. Preferred substitutions are made in residue (1-5) of β-endorphin. A most preferred D-amino acid analog is [D-Ala$^2$]-β-endorphin;-(1-5)-(16-31).

In view of the fact that the 6–15 residue of β-endorphin contains the antigenic determinant site, as determined by comparative radioimmunoassays for β-endorphin and various fragments thereof, the compounds of the present invention present less risk of inducing anaphylactic response in treated subjects than the parent compounds. The compounds of the invention have the additional advantage that they contain a substantially reduced number of amino acids thus making their synthesis quicker and less costly than the parent compounds.

Finally, and quite unexpectedly, the compounds of the invention exhibit a higher order of biological activity than the parent compounds. Thus, for example, in the guinea pig ileum bioassay of Kosterlitz et al. Brit. J. Pharmacol. 39, 398 (1970) the IC$_{50}$ (50% inhibiting concentration) of representative β-endorphins and the relative potency of β-endorphin fragments are as follows.

The IC$_{50}$ of $\beta_h$-endorphin was $2.70 \times 10^{-8}$M while $\beta_c$-endorphin had the equivalent value of $2.69 \times 10^{-8}$M. The relative potencies for the fragments and a representative compound of the invention were as follows: $\beta_h$ and $\beta_c$-endorphin, 1.00; met-enkephalin, 0.26; $\beta_c$-endorphin-(6-31), 0.04; $\beta_h$-endorphin-(1-5)-(16-31), 1.35; $\beta_c$-endorphin-(20-31), 0.001; $\beta_h$-lipotropin hormone, 0.001. Therefore, the compound of the invention $\beta_h$-endorphin-(1-5)-(16-31) was about 35% more potent in this assay for opiate agonist activity than its parent compound $\beta_h$-endorphin.

To put the above results in proper perspective it should be noted that depending on the nature of the assay procedure used, route of administration and the species of the subject animals employed, β-endorphin has exhibited from about three to about 90 times the activity of morphine on a molar basis.

The β-endorphin analogs of the present invention can be employed as opiate agonists and as analgesic agents in the same manner as their parent compounds with dosage being adjusted for their relative potencies.

Sterile, stable solid dosage forms suitable for reconstitution for parenteral administration are obtained by filtering aqueous buffered solutions of the desired compound of the invention through a sterilizing filter into sterile vials and then lyophilizing. The solid lyophilized product can be reconstituted at the time of use by the addition of sterile, isotonic saline. Other parenteral dosage forms known in the art for the administration of peptides can also be used.

EXAMPLE 1

Solid Phase Synthesis of Camel Beta-endorphin (1-5)-(16-31)

N$^\alpha$-Boc-α-Benzyl-γ-Glutamyl Benzhydrylamine Resin

Attachment of α-benzyl N$^\alpha$-t-butyloxycarbonyl glutamate to benzhydrylamine resin was performed by means of its symmetrical anhydride. A sample (2.5 g) of benzhydrylamine hydrochloride resin containing 0.38 mmol free amine per g. was neutralized with 5% diisopropylethylamine (DIEA) in CH$_2$Cl$_2$ and then treated with 3 equivalents of the symmetrical anhydride in CH$_2$Cl$_2$ for 45 min. Five ml. of 5% DIEA in CH$_2$Cl$_2$ were then added followed by an additional 10 min. reaction time. The reaction was terminated by filtration and washings with three 30 ml. portions of CH$_2$Cl$_2$ and three 30 ml. portions of absolute ethanol. After retreatment of the resin with the same amount of symmetrical anhydride, it was dried in vacuo over P$_2$O$_5$ for 1 hour. Completeness of the reaction was verified by the Gisin test. After hydrolysis of a sample in propionic acid-12 N HCl, amino acid analysis gave one peak corresponding to 0.23 mmol of Gln per g. (68% cleavage). The identification of the HF cleaved product as glutamine was confirmed by thin layer chromatography in 1-butanol-acetic acid-water (4:1:1) and 1-butanol-pyridine-acetic acid-water (6:1:1.2:4.6).

Symmetrical Anhydrides of Boc-Amino Acids

The reaction of Boc-amino acids with dicylohexylcarbodiimide was performed as follows: 1.9 mmol of Boc-amino acid in 6 ml. of methylene chloride were cooled to 0° C and mixed with 1.6 ml. of 0.6 M N,N'-dicyclohexylcarbodiimide in methylene chloride. After stirring for 20 minutes at 0° C., the precipitate of dicyclohexylurea was removed by filtration at 25° C. and washed with 2.4 ml. of methylene chloride. The filtrate was used immediately for the coupling reaction.

Protected Camel Beta-Endorphin (1-5) (16-31) Benzhydrylamine Resin

The resin just described was submitted to the following synthesis schedule:
1. Wash with three 15 ml. portions of methylene chloride (retention volume of the resin for methylene chloride was 5 ml. after filtration); (2) removal of the Boc group with 50% trifluoroacetic acid in methylene chloride for 15 min; (3) wash with two 15 ml. portions of methylene chloride; (4) wash with two 15 ml. portions of 50% dioxane in methylene chloride; (5) wash with two 15 ml. portions of methylene chloride; (6) 5 minutes of neutralization with 15 ml. of 5% diisopropylethylamine in methylene chloride; (7) wash with six 15 ml. portions of methylene chloride; (8) add the solution of preformed symmetrical anhydride of Boc-amino acid and shake for 30 min; (9) add 0.20 equivalents of 5% diisopropylethylamine in methylene chloride and shake for another 20 min; (1) wash with three 15 ml. portions of methylene chloride; and (11) wash with three 15 ml. portions of absolute ethanol. The above cycle was repeated for the following N-protected amino acids:

Boc-Gly; Boc-Lys (oBr-Z); Boc-Lys (oBr-Z); Boc-His(Boc); Boc-Ala; Boc-Asn; Boc-Lys (oBr-Z); Boc-Ile; Boc-Ile; Boc-Ala; Boc-Asn*; Boc-Lys (oBr-Z); Boc-Phe; Boc-Leu; Boc-Thr; Boc-Met; Boc-Phe; Boc-Gly; Boc-Gly; Boc-Tyr (oBr-Z).

*After introduction of Asn, the peptide resin was then carried through the same schedule for incorporation of the remaining residues with two exceptions. Two treatments with 5% DIEA in methylene chloride were used for neutralization and for the second stage of anhydride couplings, trifluoroethanol was added to a concentration of 20%.

β-Camel Endorphin (1-5) (16-31)

A sample (0.6 g.) of protected endorphin resin was submitted to deprotection and neutralization steps in order to remove the Boc group. The dried resin was then stirred in the presence of 1.8 ml. of anisole and 15 ml. of liquid HF at 0° C. for 1 hour. The HF was removed with a stream of nitrogen and the oily residue was washed with two 15-ml. portions of ethyl acetate. The peptide was extracted from the resin with three 15-ml. portions of 50% acetic acid and the combined filtrates were evaporated in vacuo to a small volume (3 to 5 ml.) and submitted to gel filtration on Sephadex G-10 (2 × 25 cm column) in 0.5 N acetic acid. One peak (280 nm detection) was detected and lyophilized. This material was then submitted to chromatography on carboxymethylcellulose. Isolation of the main peak (280 nm detection) gave the desired product. Further purification of this material was effected by partition chromatography on Sephadex G-50. Isolation of the material represented by the main peak [Folin-Lowry detection] gave highly purified beta-camel endorphin (1-5) (16-31).

Amino acid analysis after acid hydrolysis and after complete enzymic digestion (first with trypsin and chymotrypsin and then leucine amino peptidase) gave values in good agreement with theoretical.

EXAMPLE 2

Analog of beta-human-endorphin (1-5) (16-31)

The procedure of Example 1 is repeated with the exception that the resin used in chlormethylated copolystyrenedivinyl benzene resin, the carboxyl terminus group utilized is Boc-Glu (Bzl) and Boc-His(Boc) is replaced by Boc-Tyr (oBr-Z) to thereby produce $\beta_h$-endorphin (1-5) (16-31) having an amino acid sequence as follows:

H—Tyr—Gly—Gly—Phe—Met—Thr—Leu—Phe—Lys—Asn—Ala—Ile—Ile—Lys—Asn—Ala—Tyr—Lys—Lys—Gly—Glu—OH.

Amino acid analysis after acid hydrolysis gave:

$Lys_{3.8}$, $Asp_{2.1}$, $Thr_{0.9}$, $Glu_{1.0}$, $Gly_{2.9}$, $Ala_{2.0}$, $Met_{1.1}$, $Ile_{1.2}$, $Leu_{1.0}$, $Tyr_{2.0}$ and $Phe_{2.1}$.

Partition chromatography on a Sephadex G-50 column (1.76 × 46.7 cm) with n-butanol-pyridine-0.6 M ammonium acetate (5:3:10) gave $R_f = 0.54$.

Paper electrophoresis on Whatman 3MM paper with 400 V at 24° C. for 4-5 hours using pyridine acetate buffer pH 3.7 gave $R_f = 0.64$ relative to lysine. Ninhydrin was used to detect the amino acids.

EXAMPLE 3

[D-Ala$^{2}$]-$^{beta\text{-}human\text{-}endorphin}$(1-5)(16-31)

The procedure of Example 2 is repeated with the further exception that Boc-D-Ala is used in place of the last Boc-Gly to thereby produce [D-Ala$^{2}$]-$\beta_h$-endorphin-(1-5) (16-31) having an amino acid sequence as follows:

H—Tyr—D—Ala—Gly—Phe—Met—Thr—Leu—Phe—Lys—Asn—Ala—Ile—Ile—Lys—Asn—Ala—Tyr—Lys—Lys—Gly—Glu—OH.

EXAMPLE 4

Analog of beta-porcine-endorphin (1-5) (16-31)

The procedure of Example 1 is repreated with the exception that the first Boc-Ile amino acid is substituted with Boc-Val so as to thereby produce beta-porcine-endorphin (1-5)-(16-31) having an amino acid sequence as follows:

H—Tyr—Gly—Gly—Phe—Met—Thr—Leu—Phe—Lys—Asn—Ala—Ile—Val—Lys—Asn—Ala—His—Lys—Lys—Gly—Gln—OH.

I claim:

1. An analog of β-endorphin of the sequence β-endorphin-(1-5)-(16-31).
2. The analog of claim 1 which is $\beta_h$-endorphin-(1-5)-(16-31).
3. The analog of claim 1 which is $\beta_c$-endorphin-(1-5)-(16-31).
4. The analog of claim 1 which is $\beta_p$-endorphin-(1-5)-(16-31).
5. An analog of β-endorphin of the sequence [D-Ala$^{2}$]-$^{\beta\text{-}endorphin}$(1-5) (16-31).
6. The analog of claim 5 which is [D-Ala$^{2}$]-$\beta_h$-endorphin-(1-5)-(16-31).
7. The analog of claim 6 which is [D-Ala$^{2}$]-$\beta_c$-endorphin-(1-5)-(16-31).

* * * * *